United States Patent [19]

Blades

[11] 4,400,976
[45] Aug. 30, 1983

[54] ULTRASONIC TRANSCEIVER CIRCUIT FOR LEVEL SENSING
[75] Inventor: Frederick K. Blades, Boulder, Colo.
[73] Assignee: PureCycle Corporation, Boulder, Colo.
[21] Appl. No.: 165,253
[22] Filed: Jul. 2, 1980
[51] Int. Cl.³ ...................... G01F 23/28; G01N 29/00
[52] U.S. Cl. .................................. 73/290 V; 73/632; 367/99
[58] Field of Search .............. 73/290 V, 632; 367/87, 367/99, 908; 320/1; 340/7

[56] References Cited
U.S. PATENT DOCUMENTS

| | | | |
|---|---|---|---|
| 2,167,492 | 7/1939 | Sproule | 367/87 |
| 3,526,821 | 9/1970 | Thomas | 320/1 |
| 3,589,196 | 6/1971 | Van Dyck | 367/908 |
| 3,834,233 | 9/1974 | Willis et al. | 367/908 |
| 3,874,236 | 4/1975 | Reck | 73/290 V |
| 4,114,457 | 9/1978 | Thun | 73/632 |
| 4,221,004 | 9/1980 | Combs et al. | 367/908 |
| 4,222,113 | 9/1980 | Hansen | 73/632 X |

Primary Examiner—Daniel M. Yasich
Attorney, Agent, or Firm—Woodcock, Washburn, Kurtz, Mackiewicz & Norris

[57] ABSTRACT

An improved transceiver for use in ultrasonic echo-ranging systems is disclosed together with a system for its use. The transceiver comprises a capacitor to store power received from a central location during an inactive mode, and switching means to disconnect the capacitor from the power supply during the active mode. The capacitor is used both to supply power to an electrostatic transducer to generate an ultrasonic pulse and also to provide a noise free bias voltage to the transducer to enable it to receive the reflected pulse. An amplifier is provided as part of the transceiver so that long transmission lines between transceiver and controller are possible without undue noise. The power supply line can also be used as the signal transmission line and can be provided in a simple two-wire shielded cable, the other wire being used for logic level control signal transmission, thus allowing simplified multiplexing of a plurality of transceivers.

2 Claims, 4 Drawing Figures

ULTRASONIC TRANSCEIVER CIRCUIT FOR LEVEL SENSING

FIELD OF THE INVENTION

The present invention relates to an inexpensive remote three-wire transceiver for use with electrostatic transducers in ultrasonic echo-ranging systems.

BACKGROUND OF THE INVENTION

Ultrasonic echo-ranging has gained wide application in both liquid and solid particulate level sensing. Such systems typically provide a transducer positioned above the material whose level is to be measured. An ultrasonic burst at, for example, 50 kHz, is transmitted downwardly towards the material surface and reflected therefrom. The echo is received by the transducer and detected; that is, discrimination may be performed. The round-trip transit time between the transmission of the burst and the reception of the echo is directly proportional to the distance from the transducer to the material surface.

Ultrasonic ranging systems conventionally employ piezoelectric type transducers, often with a single element serving as both transmitter and receiver. A high frequency electrical pulse applied to a piezoelectric crystal causes it to vibrate, emitting an acoustic pulse; if a pressure variation is applied to the crystal, a voltage is produced. The transducer thus converts acoustic to electrical energy, and vice versa. Unfortunately, the mechanical inertia of the crystal significantly limits the performance in pulsed applications. The response is slow, and "ringing" of the crystal after transmission of the burst limits the minimum distance that can be measured.

Electrostatic "Sell type" transducers which comprise a highly flexible, partially metallic diaphragm spaced from an electrode, offer several advantages over the more conventional piezoelectric devices, while operating is an essentially similar fashion. The mass of the air moving element, the diaphragm, may be made extremely low, permitting both fast response and minimum ringing.

Such transducers, though, pose several unfamiliar interfacing problems. The element must be driven with on the order of several hundred volts for reasonable transmit energy, while an extremely well filtered dc bias must be applied to operate in the receive mode. Further, the efficiency is generally less than with conventional piezoelectric elements, thereby requiring high receiver gain, and putting additional burdens on the noise discrimination circuitry and transmission line.

It is often desirable to multiplex several transducers in a level measurement system, so that a single processing circuit may be used to, e.g., monitor the level in many tanks. With conventional piezoelectric transducers, often interfaced to with balanced lines for noise rejection, multiplexing poses several difficulties. Low signal levels, balanced lines, capacitance effects, noise and cross-talk must be carefully considered and compensated for. Often, due to the aforementioned problems, the cable lengths and number of transducers must be limited, thus diminishing the utility of such a system. Nor are such problems overcome by the direct substitution of electrostatic for piezoelectric transducers; indeed, the low signal levels and high voltage requirements of electrostatic transducers in many cases increases these difficulties.

OBJECTS OF THE INVENTION

It is therefore an object of the present invention to provide a relatively inexpensive remote, three-wire transceiver for use with electrostatic transducers in ultrasonic echo-ranging systems.

It is a further object of the present invention to provide a remote, three-wire transceiver that can be simply multiplexed in large echo-ranging systems.

Another object of the invention is to provide an improved echo ranging system.

SUMMARY OF THE INVENTION

A feature of the present invention is the capability to externally generate the high voltage transmit pulse required by electrostatic transducers at the remote transceiver via a simple logic level control line.

A further feature of the present invention is the provision of an amplifier integral with the remote transceiver, which serves to greatly increase the signal to noise level in systems with long transmission lines, thus much improving reliability.

A still further feature of the present invention is inherent noise rejection afforded by effective disconnection of the transceiver in large multiplexed systems when not in use.

In accordance with the features and objects of the invention listed above, the present invention provides a remote transceiver circuit for use with electrostatic transducers in ultrasonic ranging systems.

The transceiver comprises three functional subsystems; a switched power supply to generate the high voltage pulse required to send a ranging signal, a receive bias source, and an amplifier to increase the amplitude of the returned echo signal. The transceiver and the transducer are housed together in a portable assembly that can be mounted over the material whose level is to be measured.

A two wire shielded cable serves as the connection to the transceiver/transducer assembly. A first wire supplies power to the transceiver for both transmit power and receive bias, and additionally serves as the signal return line, while a second wire carries a logic level signal to activate the transceiver, thus initiating transmission, and the shield serves as the system ground.

In operation a transceiver is idle until a logic level transmit pulse is applied to the second wire. During the idle state, the first (power) line supplies current to charge a capacitor in the transceiver. When the transmit signal is applied to the second wire three actions occur. The incoming logic level transmit pulses are converted to high voltage pulses and applied to the transducer, to send an ultrasonic signal; the first line is effectively disconnected from the capacitor leaving only the charge that has previously accumulated; and the return amplifier is switched on for a predetermined period of sufficient duration to receive the delayed echo signal.

During the period that the receive amplifier is on, the capacitor supplies bias to the transducer. Since the capacitor is integral to the transducer assembly, and is disconnected from the power source, this bias voltage is free from noise and interference, as is required.

When the echo returns, the amplifier raises the level of the signal to a sufficient amplitude to minimize noise interference and transmits it back down the first wire to be detected and processed.

Finally the amplifier is switched off by a timing circuit carried in the transceiver, whereupon the first line is reconnected to supply current to charge the capacitor for further readings.

BRIEF DESCRIPTION OF THE DRAWINGS

The invention will be better understood if reference is made to the accompanying drawings, in which.

DESCRIPTION OF THE PREFERRED EMBODIMENTS

Figure 1:
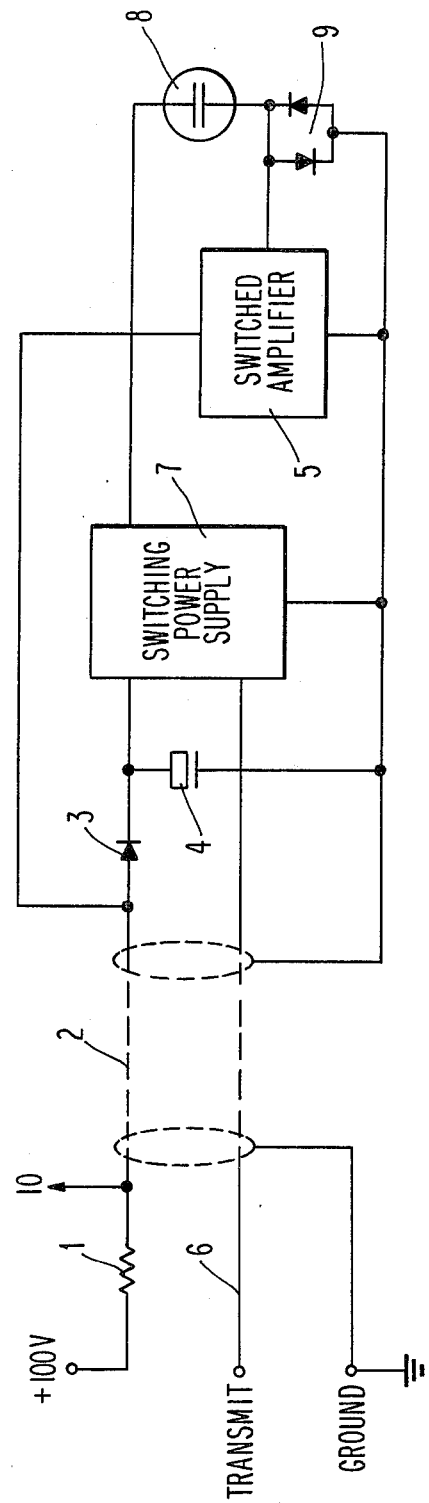
FIG. 1 is a block diagram of an ultrasonic echo-ranging transceiver built in accordance with the teachings of the present invention.

Referring now to FIG. 1, the transceiver circuitry is shown in simplified block form for clarity. The transceiver is connected to a remote power supply and controller by a two-wire shielded cable, shown in dotted lines. The voltages cited are for purposes of illustration and will vary as a function of the transducer characteristics and system requirements.

A 100 volt dc voltage source supplies current through resistor 1, power lead 2 and diode 3 to charge capacitor 4 to approximately 100 volts. Amplifier 5 is idle at during this inactive mode, drawing essentially no current from power lead 2.

To initiate a transmit/receive cycle, i.e., to enter the active mode of operation, a series of logic level pulses are applied to the control line 6 at a frequency determined in accordance with the transducer characteristics. When this occurs, a switching power supply, or inverter 7, is controlled to draw current from capacitor 4, and applies a series of high-voltage (approximately 300 volts) pulses to electrostatic transducer 8. The pulses are transformed into acoustic energy and travel downward towards the material surface.

During this transmit burst, a relatively high signal level is fed into amplifier 5 thereby causing it to turn on; clipping diodes 9 limit the input signal to a safe level. When amplifier 5 turns on, a precise amount of current is drawn from the power line 2 into amplifier 5 thereby forcing a voltage drop across the resistor 1 of approximately 10 volts and back-biasing diode 3. Amplifier 5 will remain on for a period of time sufficient to allow reception of the furthest expected echo and then automatically turn off ending the active mode. During this time capacitor 4, effectively disconnected from the power line 2 by back-biased diode 3, supplies a noise-free receive bias voltage to transducer 8.

When the echo returns, transducer 8 converts the acoustic energy into a voltage applied to the input of amplifier 5. Amplifier 5 is desirably a transconductance amplifier with a gain sufficient to produce an output of several volts across resistor 1 at the output 10. Finally, sometime following the reception of the echo, amplifier 5 automatically switches off, halting the current flow through resistor 1 and allowing diode 3 to again forward bias and recharge capacitor 4, thus readying the transceiver for the next measurement.

Figure 2:
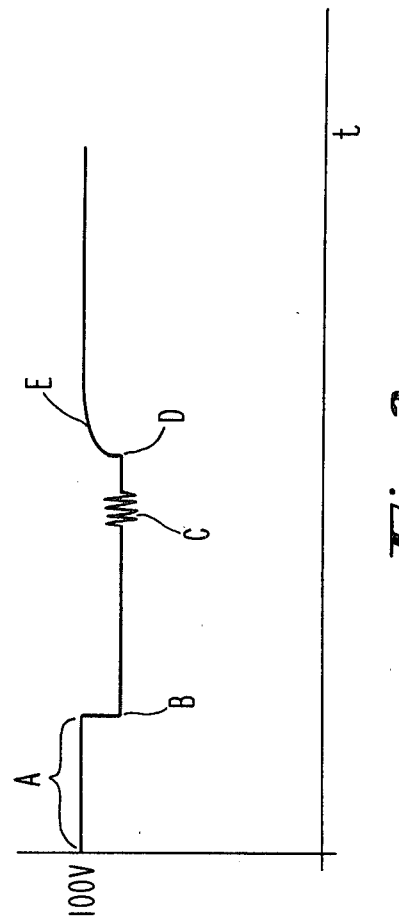
FIG. 2 is a plot in the time domain illustrating the operation of the circuit shown in FIG. 1.

Referring now to FIG. 2, the voltage at point 10 of FIG. 1 versus time is illustrated. When the capacitor is charged, the voltage remains steady at 100 v, as shown at A. When the active mode is initiated at point B, the current drawn from the amplifier 5 turning on causes the dc voltage to drop approximately 10 volts. When the echo is received, it is amplified by the amplifier 5 and outputted as a voltage signal C; the magnitude of this voltage is limited to approximately 20 volts peak to peak. A short time later amplifier 5 switches off at D, ending the active mode, unbiasing diode 3 and allowing the capacitor 4 to recharge at E and be ready to accept another transmission.

Figure 3:
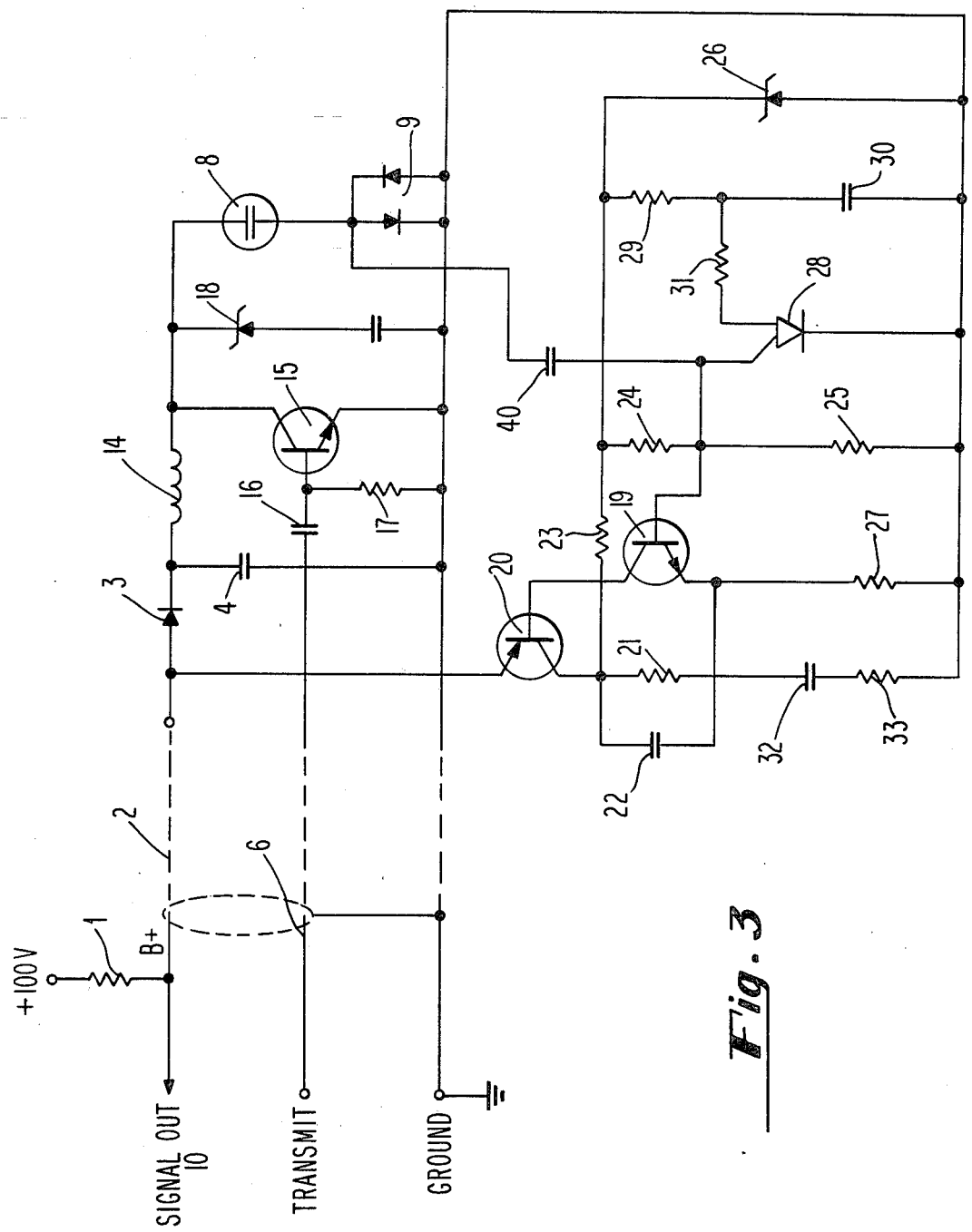
FIG. 3 is a schematic representation of a preferred embodiment of the present invention.

A preferred embodiment of the transceiver according to the present invention is shown in FIG. 3. Referring now to the upper half of FIG. 3, a switching power supply, comprising inductor 14, switching transistor 15, input capacitor 16 and resistor 17, provides the high voltage transmit pulses to transducer 8. To initiate a transmission, a series of logic level pulses, at the desired transmit frequency, are applied to the transmit or control line 6. The input capacitor 16 and the resistor 17 differentiate the incoming pulse waves, causing transistor 15 to conduct for each positive transition of the pulse train. The flyback action of inductor 14 applies high voltage pulses to the transducer 8. AC coupled zener diode 18 clips the AC amplitude of the waveform at a predetermined value for two reasons; to stabilize the output amplitude against supply and component variations, and to prevent the voltage at the transducer 8 from reaching destructive levels.

The receive amplifier, shown generally in the lower half of FIG. 3, is a self-biased, high-gain compound pair, employing both AC and DC, positive and negative feedback. The input signal is developed across and peak limited by clipping diodes 9. The onset of the high level transmit pulse burst causes transistor 19 to conduct, which in turn supplies base current to transistor 20. The positive DC feedback from resistor 21 of transistor 20 to the input bias string (resistors 23, 24 and 25), causes the amplifier to latch on in a stable DC condition within an extremely short period. Zener diode 26, the resistor bias string and the DC negative feedback developed across resistor 27, stabilize the operating point. Resistor 21 is used only to develop the bias voltage and is therefore bypassed for AC signals by capacitor 22.

When the amplifier is triggered "on", a predetermined DC current is drawn from resistor 1 thereby producing a voltage drop across resistor 1 and back biasing diode 3, effectively disconnecting the power supply line 2 from the capacitor 4. Thus for the remainder of the transmit burst and the receive cycle after the amplifier has been triggered "on", the transmit and receive bias energy is drawn solely from the storage capacitor 4.

The amplifier now remains "on" for a period sufficient to allow reception of the longest expected delayed echo. Programmable Unijunction Transistor (PUT) 28, resistor 29 and capacitor 30 form a timing network to automatically switch the amplifier "off" after this predetermined period thus: when the transmit burst triggers the bias string "on", capacitor 30 begins to charge at a rate determined by resistor 29 and the breakdown voltage of zener 26. When the voltage on capacitor 30 reaches the threshold of the PUT 28, it fires, shorting out the bias string, and thereby turning the amplifier "off". Resistor 31 is included to limit the discharge current and thus ensure turn off of the amplifier.

The overall midband AC gain of the receive amplifier when "on" is determined by the ratio of resistor 33 to the external load resistor 1. Two-pole low frequency rejection is provided by input capacitor 40 and feedback capacitor 32.

Thus, when an echo is received on transducer 8, the signal is applied to the receive amplifier through coupling capacitor 40 where it is amplified and outputted as a current modulation through external load resistor 1.

Figure 4:
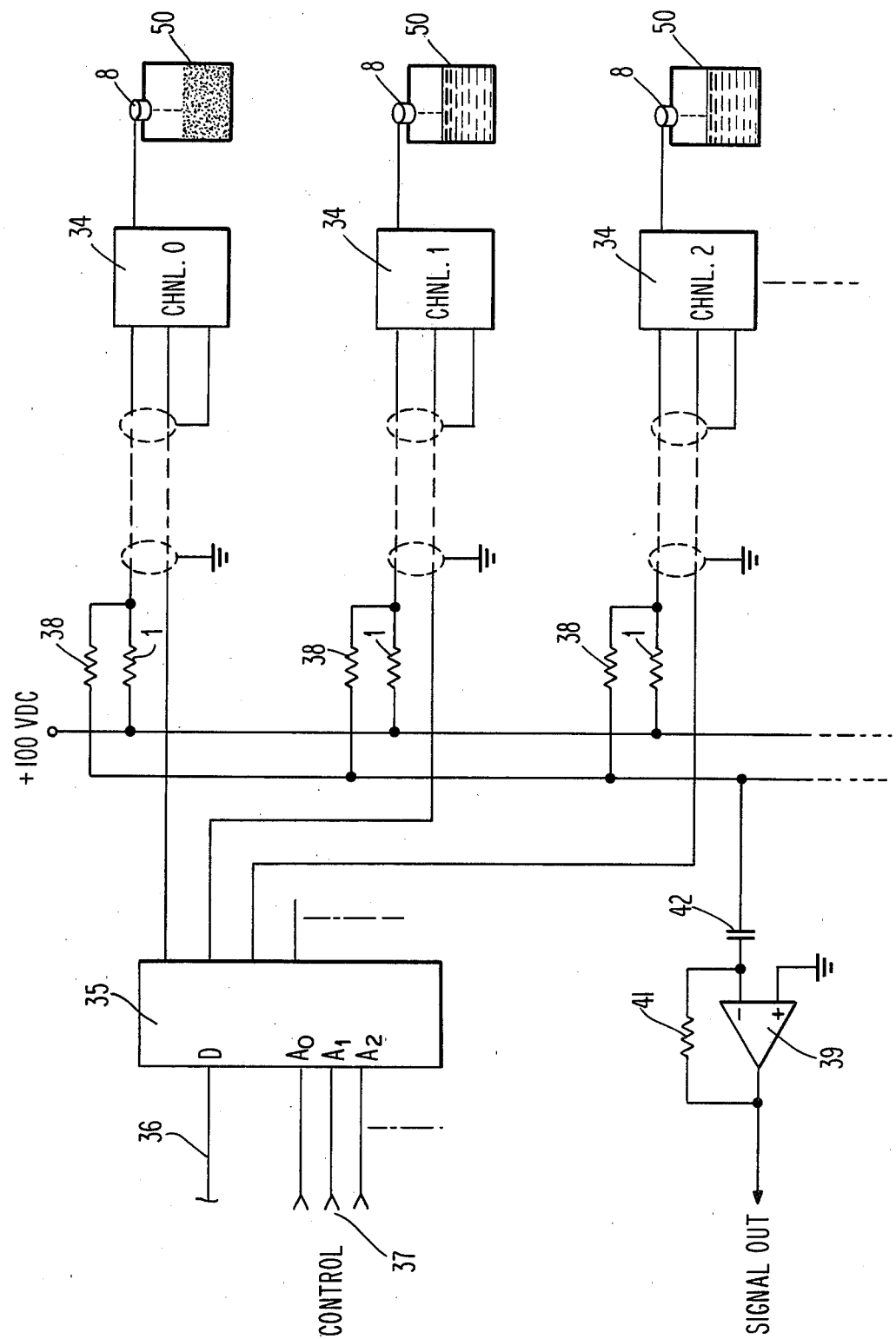
FIG. 4 is a block diagram of a multiplexed multichannel level sensing system in accordance with the teachings of the present invention.

A multiple channel multiplexed level sensing system is illustrated in simplified block form in FIG. 4. A large number of transceivers 34 according to FIG. 3 can be multiplexed by simple logic level selection of the desired channel. The transceivers 34 can be used to, e.g., monitor the level of materials in a plurality of vessels 50, and are located in proximity thereto, as shown in schematic view.

A conventional demultiplexer or control means 35 decodes the control signals $A_0, A_1, A_2 \ldots$ from a master controller to select the tank or vessel 50 whose material level is to be measured. A logic level transmit burst is applied to the data line 36 and routed according to the address applied to the demultiplexer address lines 37.

As discussed above, upon being triggered by the logic level signal burst, the selected channel transmits an acoustic burst, receives the echo, amplifies it and outputs it as a current modulation through its respective load resistor 1. The voltage output produced across the load resistor 1 of the transceiver 34 in use is then fed into mixing amplifier 39 through the corresponding mixing resistor 38 and input coupling capacitor 42, which is required to isolate the amplifier from the 100 volt DC power supply. Amplifier 39 is in a conventional mixing amplifier configuration employed to prevent interaction between channels, to level shift the output and to provide a low output impedance. The gain of this stage is equal to the ratio of feedback resistor 41 to mixing resistor 38, thus providing optionally differing gain to the differing channels. The signal can thence be passed to noise discrimination circuitry, for example as described in my copending application Ser. No. 165,254, filed July 2, 1980, now U.S. Pat. No. 4,315,325, or other processing circuitry.

The advantages of the present invention over a more conventional approach may now be cited explicitly:

First, by multiplexing signal and power in one line, the interface is accomplished with a simple two-wire shielded cable, thereby reducing expense and bulk.

Second, the high voltage, high frequency pulses required for transmission are generated at the transducer, thereby eliminating the problems associated with transmitting high voltage, high frequency signals down long cables; the high voltage transmission is dc, while the high frequency transmission is logic level.

Third, the storage capacitor, since it is effectively disconnected from the transmission line during the receive mode, supplies noise-free receive bias to the transducer. With a typical difference in transmit/receive signal levels of several orders of magnitude and the well known bias supply noise susceptibility of electrostatic transducers, this fact offers a simple solution to the problem of providing noiseless bias in systems requiring multiple transducers in remote level sensing sites.

Fourth, the signal is amplified at the transducer location, thus allowing long transmission lines.

Fifth, the transmit cycle is initiated with a simple logic level signal. This permits multiplexing of a large number of transducers with simple logic level selection.

Sixth, each signal/power transmission line is effectively AC grounded through the storage capacitor when not in use, thereby reducing the noise which may be induced by unused channels in a multiplexed system.

Seventh, the output signal is a current, thereby unaffected by transmission line losses.

Eighth, and finally, the extensive use of feedback stabilizes the circuit against temperature and age-induced component drift, power supply variation and in many cases negates the need for initial calibration.

It will be appreciated that there has been described a transceiver for use in ultrasonic echo-ranging system and a system within which it can be used, which provides numerous advantages over the prior art. Moreover, it will be appreciated by those skilled in the art that the circuitry described has wide applicability to echo-ranging systems, particularly those wherein it is desired that a long distance be interposed between individual transceivers and a central controller such as frequently encountered in, e.g., chemical plants and various sorts of industrial manufacturing operations, as well as in monitoring of, for example, aircraft fuel levels. Of course, use of the term "distant" or "remote" is not to be construed as a limitation on the invention; the "distance" could be fractional. It will likewise be appreciated by those skilled in the art that numerous modifications and improvements can be made to the preferred embodiment of the invention disclosed above without departing from its essential spirit and scope, which should therefore not be construed as limited by the above specification but only by the following claims.

What is claimed is:

1. A system for monitoring the level of materials contained in one or more vessels, comprising:
   one or more remote transducers connected to respective transceivers and located at said vessels;
   a central controller for providing control signals and energy to said transceivers and for receiving signals from said transceivers and converting said received signals into signals indicative of the level of materials in said vessels; and
   conductor means connecting said transceivers and said controller at a distant location from said vessels, each of said transceivers selectively activated for operating in a first quiescent mode and a second active mode, the transition from said first to said second modes being initiated by control means at said distant location, each said transceiver comprising:
   capacitor means connected to said conductor means during said first mode for storage of energy provided from said distant location;
   means for effectively disconnecting said capacitor means from said conductor means at the time of transition from said first to said second mode;
   power supply means for applying energy stored in said capacitor to said transducer to cause an ultrasonic signal to be emitted therefrom;
   electrostatic means for detecting the reflected ultrasonic signal, said means being biased for detection by energy stored in said capacitor means;
   means for amplifying said detected signal and transmitting said amplified signal over said conductor means; and
   means for reconnecting said capacitor means to said conductor means at the end of said second mode.

2. The transceiver of claim 1 further comprising means for controlling the duration of said second mode.

* * * * *